(12) United States Patent
Longmire et al.

(10) Patent No.: US 11,450,415 B1
(45) Date of Patent: Sep. 20, 2022

(54) METHODS AND SYSTEMS FOR HEALTH INSURANCE PORTABILITY AND ACCOUNTABILITY ACT APPLICATION COMPLIANCE

(71) Applicant: Medable Inc., Palo Alto, CA (US)

(72) Inventors: Michelle Rae Longmire, Palo Alto, CA (US); Timothy Robert Smith, Palo Alto, CA (US); James Marcel Sas, Palo Alto, CA (US)

(73) Assignee: Medable Inc., Palo Alto, CA (US)

( * ) Notice: Subject to any disclaimer, the term of this patent is extended or adjusted under 35 U.S.C. 154(b) by 0 days.

(21) Appl. No.: 15/132,146

(22) Filed: Apr. 18, 2016

Related U.S. Application Data

(60) Provisional application No. 62/149,486, filed on Apr. 17, 2015.

(51) Int. Cl.
   *G16H 10/60* (2018.01)
   *G06F 11/14* (2006.01)
   *G06F 21/62* (2013.01)
   *G06F 21/44* (2013.01)

(52) U.S. Cl.
   CPC .......... *G16H 10/60* (2018.01); *G06F 11/1451* (2013.01); *G06F 21/44* (2013.01); *G06F 21/6245* (2013.01); *G06F 2201/80* (2013.01)

(58) Field of Classification Search
   CPC ....... H04L 63/20; H04L 41/16; G06F 19/366; G06F 9/45558; G06F 21/6245; G06F 11/1451; G06F 21/44; G06F 2201/80; G06Q 10/10
   USPC .......................................................... 726/3
   See application file for complete search history.

(56) References Cited

U.S. PATENT DOCUMENTS

| | | | | |
|---|---|---|---|---|
| 7,885,943 B1 * | 2/2011 | Yehuda | ........... | G06Q 10/10 707/665 |
| 8,874,685 B1 * | 10/2014 | Hollis | ........... | H04L 41/00 709/206 |
| 9,645,628 B1 * | 5/2017 | Loafman | ........... | G06F 1/3206 |
| 2001/0034618 A1 | 10/2001 | Kessler | | |
| 2002/0010679 A1 | 1/2002 | Felsher | | |

(Continued)

FOREIGN PATENT DOCUMENTS

WO    WO-2012162596 A1 * 11/2012 ........... A61B 5/0013

*Primary Examiner* — Bryan F Wright
(74) *Attorney, Agent, or Firm* — Cesari and McKenna, LLP

(57) ABSTRACT

Methods and systems for determining whether a software application that is executable by an electronic device is compliant under the Health Insurance Portability and Accountability Act (HIPAA) are provided. A software application is accessed over a network. A programmed computer processor is used to determine whether said software application, upon execution, is at or above an (i) access control threshold, (ii) audit control threshold, (iii) data integrity threshold, (iv) authentication threshold, and (v) transmission security threshold, which thresholds are minimum thresholds for HIPAA compliance. Additionally, a determination that said software application is HIPAA compliant is made if said software application, upon execution, is at or above (i) said access control threshold, (ii) audit control threshold, (iii) data integrity threshold, (iv) authentication threshold, and (v) transmission security threshold. Further, a determination as to whether said software application is HIPAA compliant is output.

21 Claims, 8 Drawing Sheets

(56) References Cited

U.S. PATENT DOCUMENTS

| | | | |
|---|---|---|---|
| 2002/0107875 A1* | 8/2002 | Seliger | G06F 21/6218 |
| 2003/0004754 A1* | 1/2003 | Krutz | G16H 10/60 |
| | | | 705/2 |
| 2003/0050803 A1* | 3/2003 | Marchosky | G16H 10/60 |
| | | | 705/3 |
| 2004/0054918 A1* | 3/2004 | Duri | G06Q 20/382 |
| | | | 726/1 |
| 2004/0098285 A1* | 5/2004 | Breslin | G06Q 10/10 |
| | | | 713/193 |
| 2004/0172558 A1* | 9/2004 | Callahan | H04L 63/08 |
| | | | 726/2 |
| 2004/0193907 A1 | 9/2004 | Patanella | |
| 2006/0026042 A1 | 2/2006 | Awaraji | |
| 2006/0075401 A1* | 4/2006 | Smegner | G06F 8/65 |
| | | | 717/174 |
| 2006/0123101 A1* | 6/2006 | Buccella | G06F 21/552 |
| | | | 709/223 |
| 2008/0271110 A1* | 10/2008 | Graves | G06Q 10/10 |
| | | | 726/1 |
| 2011/0047135 A1* | 2/2011 | Vizethann | G06F 19/366 |
| | | | 707/705 |
| 2012/0216243 A1* | 8/2012 | Gill | G06Q 10/063 |
| | | | 726/1 |
| 2014/0331276 A1* | 11/2014 | Frascadore | H04L 63/20 |
| | | | 726/1 |
| 2015/0058997 A1* | 2/2015 | Lee | G06F 9/45558 |
| | | | 726/26 |
| 2016/0373289 A1* | 12/2016 | Hernandez | H04L 41/16 |
| 2019/0096511 A1* | 3/2019 | Longmire | G16H 10/20 |

* cited by examiner

METHODS AND SYSTEMS FOR HEALTH INSURANCE PORTABILITY AND ACCOUNTABILITY ACT APPLICATION COMPLIANCE

CROSS-REFERENCE TO RELATED APPLICATIONS

This application claims the benefit of U.S. Provisional Patent Application Ser. No. 62/149,486 entitled "Methods and Systems for Health Insurance Portability and Accountability Act Application Compliance," filed Apr. 17, 2015, the disclosure of which is hereby incorporated by reference in its entirety.

BACKGROUND

The Health Insurance Portability and Accountability Act of 1996 was enacted by the United States Congress and signed into law in 1996. Title I of HIPAA regulates the availability and breadth of group health plans and certain individual health insurance policies. It amended the Employee Retirement Income Security Act, the Public Health Service Act, and the Internal Revenue Code. Title I requires the coverage of and also limits restrictions that a group health plan can place on benefits for preexisting conditions. Group health plans may refuse to provide benefits relating to preexisting conditions for a period of 12 months after enrollment in the plan or 18 months in the case of late enrollment. Title I allows individuals to reduce the exclusion period by the amount of time that they had "creditable coverage" prior to enrolling in the plan and after any "significant breaks" in coverage. "Creditable coverage" is defined quite broadly and includes nearly all group and individual health plans, Medicare, and Medicaid. A "significant break" in coverage is defined as any 63 day period without any creditable coverage. Along with an exception, allowing employers to tie premiums or co-payments to tobacco use, or body mass index.

SUMMARY

The present disclosure provides methods and systems for determining whether a software application, such as a mobile application, that is executable by an electronic device is compliant under the Health Insurance Portability and Accountability Act (HIPAA). In examples, a HIPAA-compliance platform may be used to assess whether particular applications is compliant with HIPAA. Such methods and systems may automatically enable an application that is not HIPAA compliant to become HIPAA compliant. Additional aspects discussed herein include data analysis characteristics, as well as integration components that allow users to make use of data analysis. Tools that may be helpful for application developers include data analysis and data integration tools.

In one aspect, a method for determining whether a software application that is executable by an electronic device is compliant under the Health Insurance Portability and Accountability Act (HIPAA) is provided. The method comprises accessing said software application over a network. The method also comprises using a programmed computer processor to determine whether said software application, upon execution, is at or above an (i) access control threshold, (ii) audit control threshold, (iii) data integrity threshold, (iv) authentication threshold, and (v) transmission security threshold, which thresholds are minimum thresholds for HIPAA compliance. Additionally, the method comprises determining that said software application is HIPAA compliant if said software application, upon execution, is at or above (i) said access control threshold, (ii) audit control threshold, (iii) data integrity threshold, (iv) authentication threshold, and (v) transmission security threshold. The method also comprises outputting a determination as to whether said software application is HIPAA compliant.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The present disclosure provides methods and systems for determining whether a software application, such as a mobile application, that is executable by an electronic device is compliant under the Health Insurance Portability and Accountability Act (HIPAA). Such methods and systems may automatically enable an application that is not HIPAA compliant to become HIPAA compliant.

HIPAA compliance aspects of the present disclosure may include a number of technical safeguards with respect to objects of an application. As used herein, an "object" may be considered as an Account, Team, Conversation and Patient File. Many standard objects can be extended by augmenting their default access controls and by adding custom properties. Extensible objects can also have custom feed definitions, enabling posts. Custom object definitions can also be created, with their own set of custom properties, feed definitions, and access controls. Additionally, in the scope of our documentation a "context" may be an instance of an Object. For example, a user account may be a context of an Account. When the present disclosure refers to a context's properties or to a context's access control list, the context may be regarded as a concrete instance of an object definition.

In additional aspects, objects can be customizable. In particular, a user may extend the API by creating new objects and extending the standard objects using an administration interface. All custom objects automatically inherit the technical safeguards outlined above. At each access level, custom objects and properties may be prefixed with c_ to differentiate them from standard properties that may be placed alongside in a document. For example, retrieving a custom property from a custom object might look like GET/c_records/551ebec0f6b25fd828742de1/c_info. In additional examples, Standard Object properties may not be modified, though new properties may be added to those marked as extensible. Additionally, and some of the object's configuration can either be overriden or extended, including the access control list.

Figure 1:
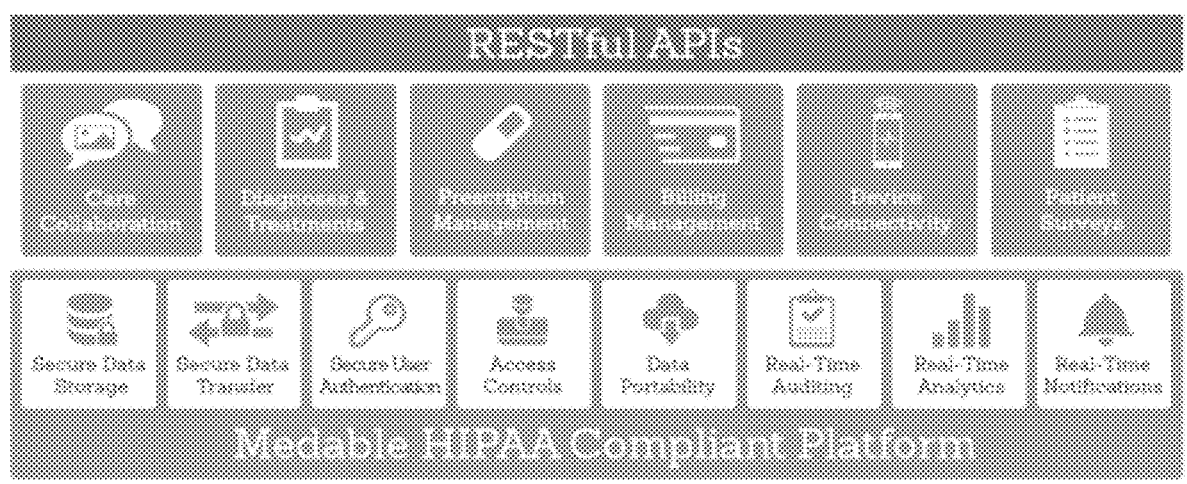
FIG. 1 shows a HIPAA compliant platform API, in accordance with embodiments of the invention.

Technical safeguards with respect to objects may include access controls, audit controls, data integrity, person or entity authentication, and transmission security. Technical safeguards discussed herein may be used to assess particular applications for HIPAA compliance. Additionally, particular applications may integrate technical safeguards as discussed herein to obtain benefits of the particular safeguards. Accordingly, application developers may use a HIPAA compliance platform, such as HIPAA compliant platform as illustrated in FIG. 1, in developing HIPAA-compliant applications.

Access controls are used in the process of providing only authorized persons access to protected health information (PHI) and/or personally identifiable information (PII). Audit controls are used by an application to keep track of system and user access to PHI data. Data integrity is used by persons and entities take reasonable steps to ensure that individually identifiable health information is complete, accurate, and up-to-date to the extent necessary for the person's or entity's intended purposes and has not been altered or destroyed in an unauthorized manner. Regarding person or entity authentication, an application may implement procedures to verify that a person or entity seeking access to electronic protected health information is the person or entity claims. Additionally, transmission security may be used by an application to ensure that there are secure protocols for communication. The present disclosure provides methods for enabling HIPAA compliance and compliant functionality to applications and devices and to the users of those applications by automatically and transparently enforcing technical safeguards via a RESTful application programming interface (API), as shown in FIG. 1. In examples, different APIs may be used. The way customers interact with the HIPAA-compliance platform as discussed herein may be governed by a RESTful API standard, or may be governed by another type of API. Additional APIs may include a simple object access protocol (SOAP) API. In further examples, HL7 messages may be sent back and forth to allow users to interact with the HIPAA-compliance platform discussed herein. Other mechanisms for interfacing with the platform may include Extensible Messaging and Presence Protocol (XMPP), remote procedure call (RPC).

A first example of a technical safeguard that may be used to ensure HIPAA compliance is access control. Access controls may be implemented in a number of ways, including unique user identification, emergency access procedure, automatic logoff, encryption/decryption, and access control lists. In examples, access controls may include examples of unique user identification. Unique user identification may be used to ensure that a named authenticated user is provided when accessing portions of the platform used in examples of the invention. Unique user identification may include identifying each user with a unique ID, email address, token, and/or a mobile number. Other unique identifiers could include phone or fax numbers, SSN numbers, license numbers, medical record numbers, device identifiers/serial numbers, biometric identifiers, such as fingerprint or voiceprint, employee Id's, National Provider Identifiers (NPI), or any other number or identifier generated from a combination of these identifiers or characteristics of the user. In additional examples, a unique user identification may be based on uniquely identifying devices using a device fingerprint. In particular, metadata and contextual data such as an IP address, metadata in a request, browser identifying information, and other information associated with a user and/or device may be used in authenticating purposes.

Access controls may also include one or more emergency access procedures. Emergency access procedures may be used to ensure that customers/patients are able to gain access to their medical information even if there has been an emergency at their medical site. As such, emergency access procedures may include replicating data in multiple geographically disparate data centers. Emergency access procedures may also include continuous, incremental backups and daily snapshots. In examples, incremental backups may occur every 4 hours. In some examples, service license agreements may require that data recovery is accessible in less than four hours under normal conditions, and may require that data recovery is accessible in less than 48 hours under disaster conditions.

Access controls may also include an automatic logoff aspect. In particular, applications that are being developed for HIPAA compliance may add a component of a platform-wide session timeout that is configurable by each organization that is using the HIPAA compliance platform to develop their application.

Additionally, access controls may include encryption and decryption aspects, such as using transport encryption on file systems, such as AES-256 (e.g., for use with data volumes, swap files, etc.). In some examples, a HIPAA-compliance platform as discussed herein may have each object within the platform encrypted. In this way, when data that is used in the application or data written to files is encrypted, the risk of a data breach may be limited when the information that may be encountered is encrypted. Additional examples of encryption and decryption aspects may include hardened, encrypted external key servers (such as a remote software security module (RSSM); SSL from external interface to clients; internet traffic over SSL; SSL-only to clients with CA signed certificates; SSL-only between internal endpoints with self-signed certificates; and encryption keys maintained securely and separately from data; and SLL certificate authentication such as an X509, internally. In some examples, the encryption and decryption aspects as discussed herein may be used to protect data in transit, such as when data is being transitioned from a mobile terminal to the cloud, and may also be used to protect data when the data is at rest, such as when the data is written at a database or a written file.

Figure 5:
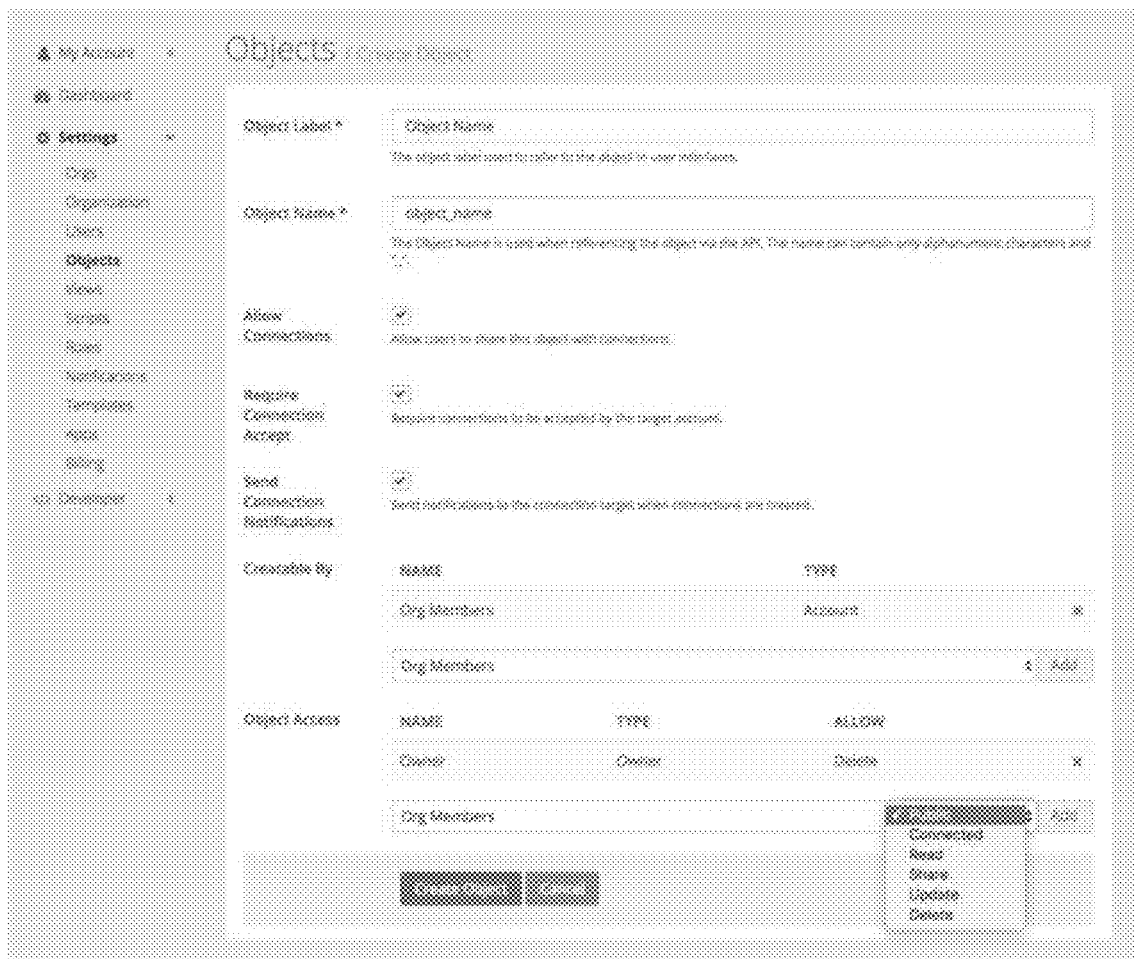
FIG. 5 shows a screen shot that illustrates a graphical user interface for specifying a default access control list access level, in accordance with embodiments of the invention.

Access levels may be used to allow fine-grained access to protected health information. Access may be pessimistic by nature, and access may be granted to objects and their properties at the user role, group or account level. FIG. 5 shows a screen shot that illustrates a graphical user interface for specifying a default access control list access level, in accordance with embodiments of the invention. The following table describes the assignable access levels:

| Level | Name | Description |
| --- | --- | --- |
| 1 | Public | A principal with this access can scan public details (for example, an organization logo) |
| 2 | Connected | Granted when making Connections, and typically provides read access to context properties. |
| 3 | Reserved | |
| 4 | Read | Grants access to private context properties. For example, accounts get read access to themselves and can read the account's email property. |
| 5 | Share | Those with share access can create connections to a context using object's Share Chain |
| 6 | Update | Update access typically provides write access to context properties. Write access may include the ability to edit context properties. |
| 7 | Delete | Grants access to delete/archive a context. |

Access levels, such as those seen above, may provide different levels of access to users or entities. While the access levels seen above include seven levels (including one reserved level), different systems may have different numbers of access levels. For example, different systems may have access levels of 1, 2, 3, 4, 5, or 6 access levels. In additional examples, different systems may have access levels of 8, 9, 10, 12, 14, 16, or more than 16 access levels.

Access control lists (ACLs) may allow each object to have its own set of default rules that determine the level of access users get to contexts (e.g., object instances). For example, an Account object default ACL may allow the account holder to update access to themselves. Additionally, owners of patient files, conversations, and teams may be granted Delete access, etc. Depending on the object, these defaults can be augmented or even overwritten in extensible standard objects. In examples, ACLs can be configured to be changeable, so the client (e.g., an application developer) can reconfigure the roles and the extent of access associated with each role based on business rules that are particular to that client.

Figure 3:
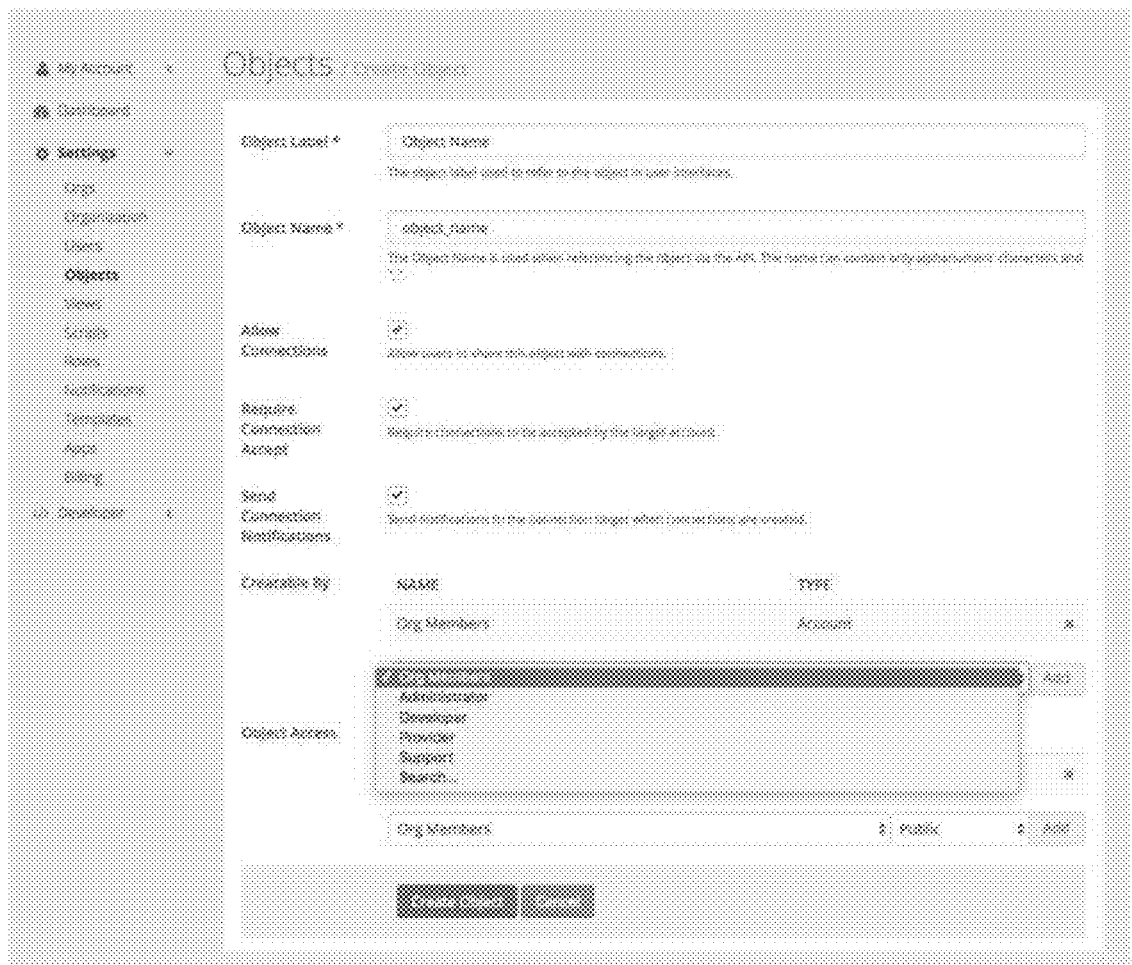
FIG. 3 shows a screen shot that illustrates a graphical user interface for adding a create access control list to an object, in accordance with embodiments of the invention.
Figure 4:
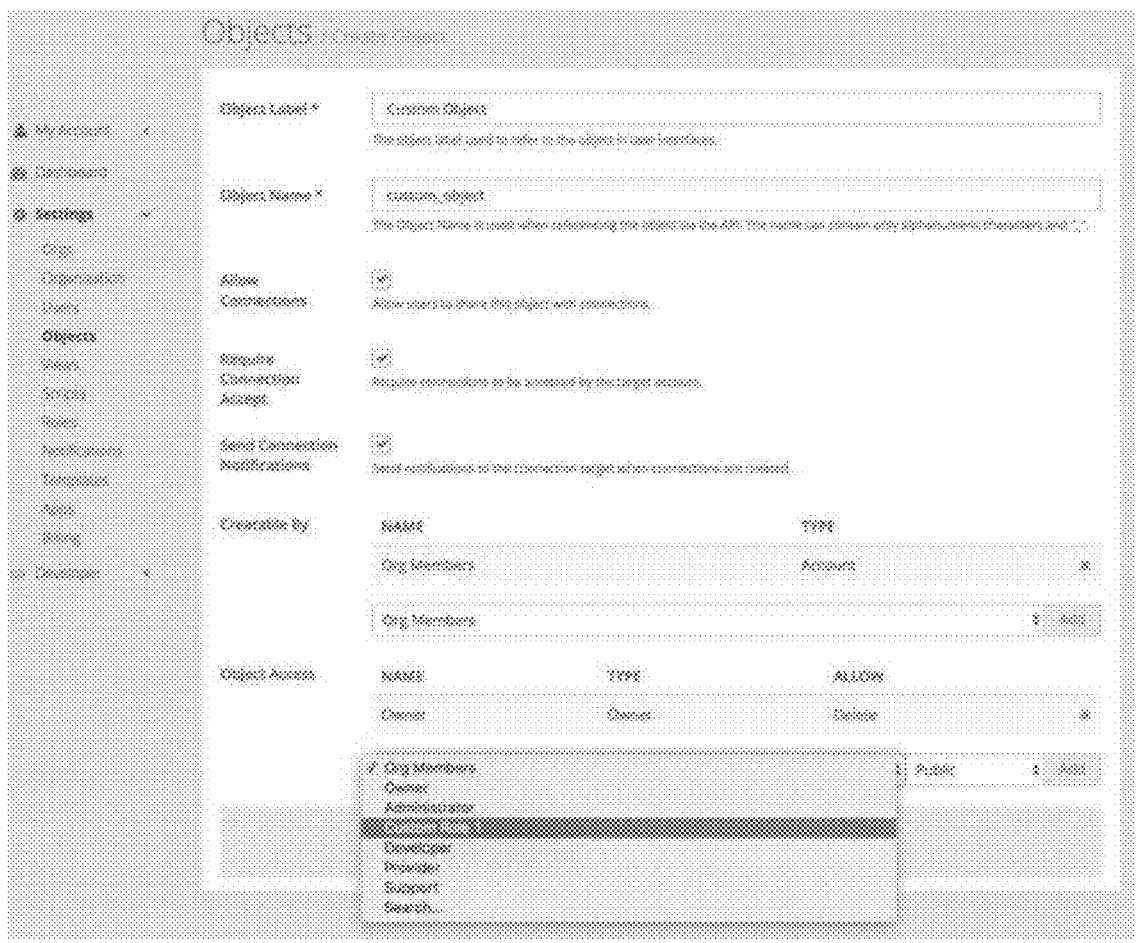
FIG. 4 shows a screen shot that illustrates a graphical user interface for adding a default access control list to an object, in accordance with embodiments of the invention.

Additionally, create ACLs may be used to determine who in an organization can create new context object instances. In some examples, conversations can only be created by accounts with the provider role. As with default ACLs, an object's create ACL can be augmented or even overwritten in extensible standard objects. FIG. 3 shows a screen shot that illustrates a graphical user interface for adding a create access control list to an object, in accordance with embodiments of the invention. Additionally, FIG. 4 shows a screen shot that illustrates a graphical user interface for adding a default access control list to an object, in accordance with embodiments of the invention.

In another aspect of the invention, share chains may be used to manage access to protected data. In particular, audit controls may be beneficial to ensure that when a user of an organization shares data with another entity, the sharing mechanism does not expose the larger organization to a data breach. Additionally, audit controls may be beneficial to ensure that when a user shares data with another entity that the correct amount of information is shared. In some examples, when a user is sharing information to a first entity and the information is then passed to a second entity, the access to the information may be more limited between the first entity and the second entity rather than between the user and the first entity. In some examples, access to information may be restricted out further as information is shared to more distant entities. In particular, a distance of a particular entity from a user may be measured by the number of connections between a user and an entity. In one example, a user having a particular access level, such as access level 5, may be able to share information that is only able to be further shared at a level that is one less than the originating level. In this example, a user having an access level of 5 may share information that at best may be further shared at an access level of 4 (or below). In this way, the sharing of information may not be propagated without restriction, but rather, may be further and further restricted as the information moves farther from the originating point.

In examples, a share chain for each object may control the access level that can be granted to a user through a connection. A user with enough access to create a connection can grant any level of access in the object's share chain as long as it is lesser than their own. For example, a user who creates a patient file may be granted Delete access through the object's default ACL. That use can then grant others share or connected access to the context. Subsequently, a connected invitee with share access could re-share the context with others, but only grant connected access. In some examples, the share chains for each object are listed in their descriptions.

Figure 2:
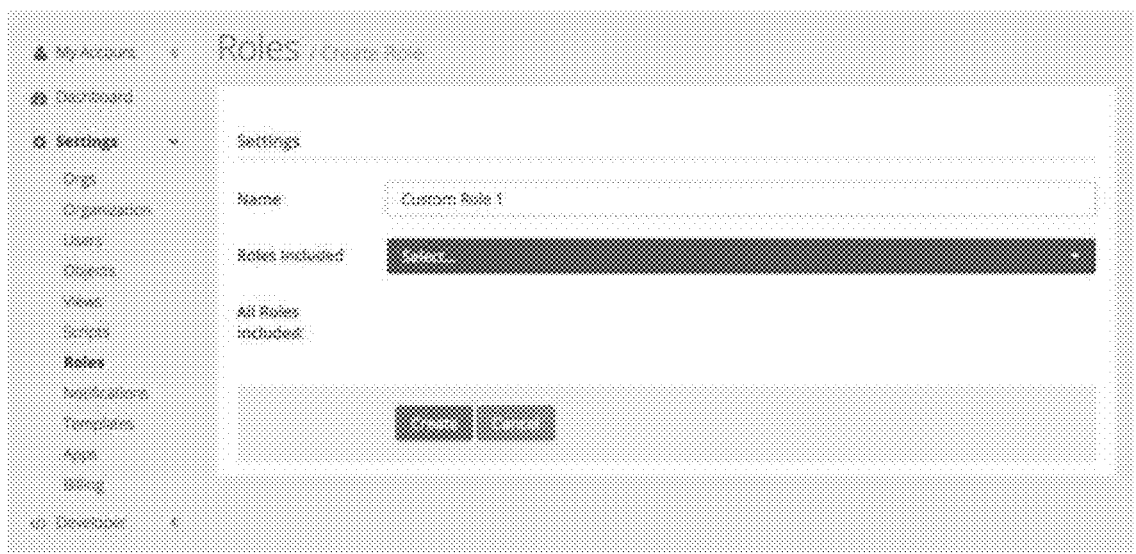
FIG. 2 shows a screen shot that illustrates a graphical user interface for adding custom roles, in accordance with embodiments of the invention.

In some examples, access control that is granted to a particular user may be based on the organizational role of that particular user. In some examples, there may be four types of organizational roles: Administrative, Support, Provider, and Developer. Additionally or alternatively, an organization can create custom roles, and can assign access controls to these. FIG. 2 shows a screen shot that illustrates a graphical user interface for adding custom roles, in accordance with embodiments of the invention. Custom roles can also be included within each other. In some examples, when a user holds a particular role, the user may also be assumed to hold additional roles that are included in the particular role. Additional roles may include a pharmacist role, a caregiver role, a family member role, and additional types of roles that may grant access to particular types of access to patient data. The custom roles may be used to systematically grant access rather than having to limit particular data using a share chain. Further, custom roles may be used to provide roles in particular contexts that are provided on a systematic level.

Figure 6:
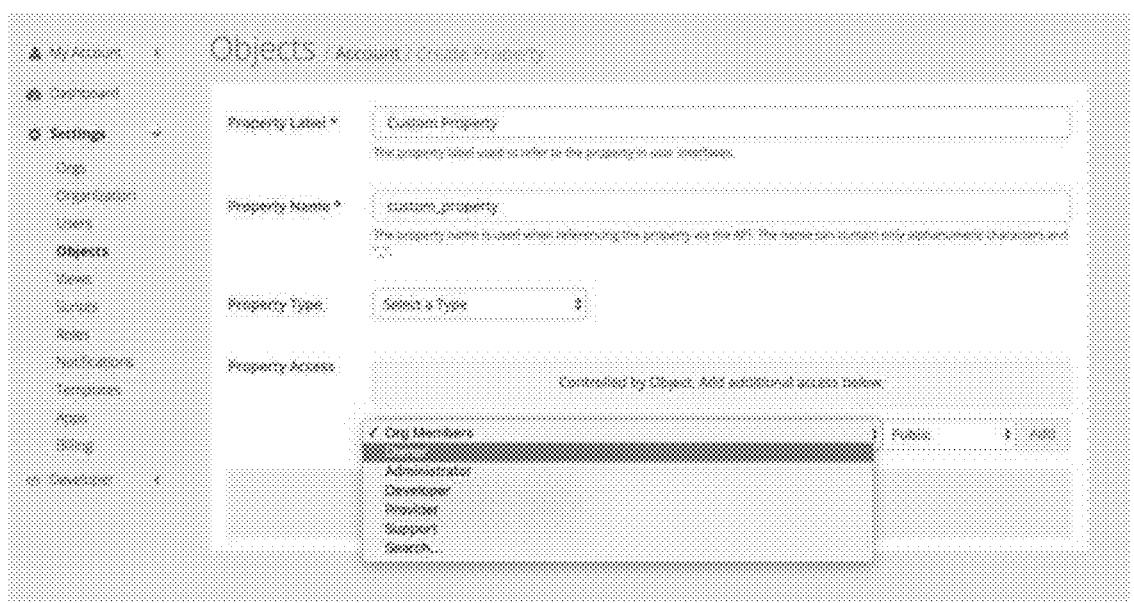
FIG. 6 shows a screen shot that illustrates a graphical user interface for adding a property access control list, in accordance with embodiments of the invention.
Figure 7:
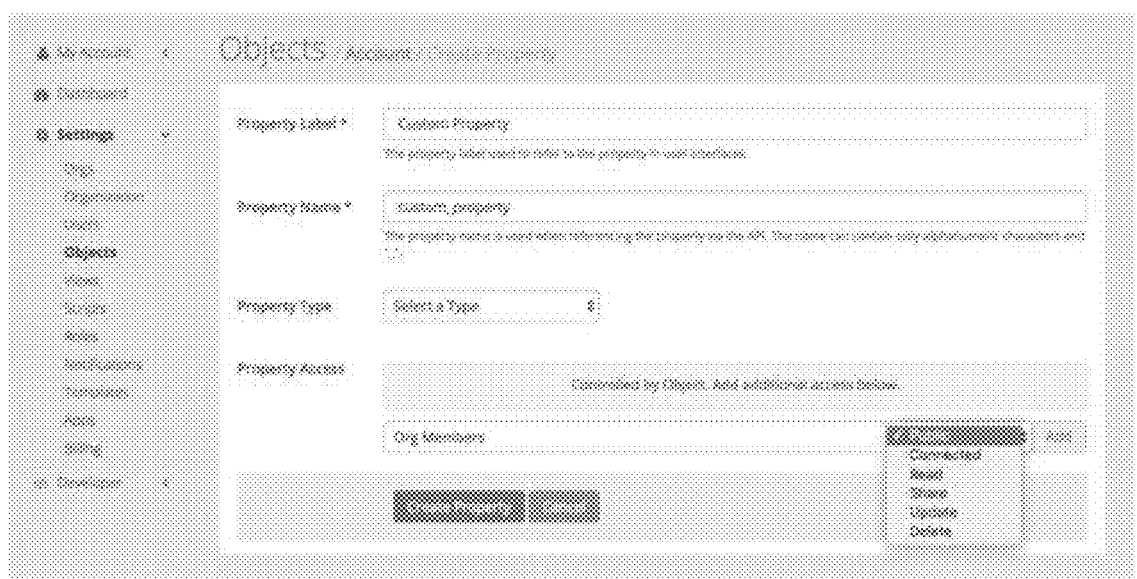
FIG. 7 shows a screen shot that illustrates a graphical user interface for adding a property access control list access level, in accordance with embodiments of the invention.

In further examples, property access control lists may be used to determine additional control of objects. FIG. 6 shows a screen shot that illustrates a graphical user interface for adding a property access control list, in accordance with embodiments of the invention. An object may be a container for data or functionality, and in examples, an object may be a data table. Further, a property of an object may be an individual field of data within the object. For example, when an object is a patient record object, there may be a number of different types of information that may be properties of the patient record object (e.g., patient name, medication, gender, age, etc.). Given the different types of information that may be available within a given object, a user may restrict and/or customize access to particular properties and/or to particular objects. In this way, object properties may have access control lists that determine the access required to create, read, update and delete properties. In examples, an organization can also augment read and update access settings for individual properties with custom ACLs. Commonly, properties required Connected access to read and Update access to update. FIG. 7 shows a screen shot that illustrates a graphical user interface for adding a property access control list access level, in accordance with embodiments of the invention.

Another example of objects having particular properties may include a pharmacy object that includes information associated with prescriptions for a patient. In examples, a pharmacy object may include a patient name property, a prescription drug property, a dosage property, and other examples of information that is useful for particular pharmaceutical objects. While patient medical record objects and pharmacy objects are provided as examples herein, objects may be used and expanded to cover additional collections of information that may be useful and beneficial during the course of patient care and, as such, may be desirable as being HIPAA-compliant.

A second example of a technical safeguard that may be used to ensure HIPAA compliance is audit control. In particular, audit controls may require the recording and examination of all activity within information systems. By using audit controls, a HIPAA-compliant platform as described herein may control access to data automatically recorded for all create, read, update, and delete operations. Examples of log entries may include an access start date, an access end date, an organizational ID, an application ID, a session ID, a client Id, a user Id, a device Id, an IP address, a request URI, a status, an API route, URL parameters, a Delta operation (for PUT), and an error (if applicable). In examples, an audit API may be available for real-time access to activity logs. In additional examples, audit logs may be continuously monitored. In particular, audit logs may be continuously monitored for anomalies automatically. In further examples, additional events that may be logged include network access and events; system access and events; application access and API request; and custom script transactions.

A third example of a technical safeguard is data integrity. In particular, data integrity might include a mechanism to authenticate electronic protected health information. The mechanism may be used to ensure that data has not been altered or destroyed. Additionally, transparent encryption may be used to prevent forced data manipulation. E-tags may also be used for data integrity. In particular, E-tags on files may be used based on file content for cache verification. Further, signed requests for file uploads and downloads may also be used to ensure data integrity. In an additional example, forced data manipulation may be prevented via file-system level encryption, such as the types of encryption discussed above. Additionally, checksums may be used at a property level and/or blob storage. In particular, a checksum, or hash, is a signature that is generated from a larger set of data. If the larger set of data changes, the signature would also change, so this can be used systematically to verify that data has or has not been modified since the previous checksum was generated.

A fourth example of a technical safeguard is person or entity authentication. In particular, person or entity authentication safeguards may be used to implement procedures to verify that a person or entity seeking access to an ePHI is the one claimed. Examples of mechanisms for person or entity authentication include Secure, HTTPOnly, Digitally signed cookies for session and device fingerprints. Additionally, a unique fingerprint may be generated for each new device and/or location detected at a sign-in. Further, automatic two-factor authentication may be provided. In particular, a verification code may be delivered via a SMS to a mobile device provided in user registration. The verification code may be a single-use verification code. Additionally or alternatively, the verification code may have a time-out function, such as a ten-minute time-out. In this way, authentication may be session-based, and signature-based authentication. Within each organization, applications can be created which provide the necessary key and secret for API access. Each application can support session-based and/or signature-based authentication.

In some examples, session-based authentication may be used. An example of a session-based authentication may be for a client application, such as an iOS app, whereby individual users authenticate using their credentials to initiate a new session. The session may be unique to the authenticated user and will timeout after a period of inactivity, based on organizational settings.

In some other examples, signature-based authentication may be used. When using signature-based authentication, a signing key may allow a third-party to make privileged calls to the API using a secure request signing mechanism. These keys can be configured for single or multiple user accounts, timed expiry, etc. Such a mechanism can be useful for scenarios such as back-end system integrations (e.g. Integrations with an EMR, or HL7 messaging appliance). Examples of signed request headers leveraged are outlined in the below table:

| Name | Description |
| --- | --- |
| Client-Signature | The calculated request signature. |
| Client-Timestamp | Client Unix Timestamp in milliseconds. The server issues a Server-Time response header with each operation which clients can use to synchronize. |
| Client-Nonce | A client-generated nonce matching /^[a-z\d]{16}$/i, used to prevent replay attacks. |
| Client-Account | Optionally sets the calling principal by account id (if the application is configured to allow principal override). |

Authentication may occur through a number of methods, including unique device fingerprint and automatic two-factor authentication. Two-factor authentication may include a verification code that is delivered via SMS. Additionally or alternatively, the verification code may use a single-use token. The token may have a time-out period, such as a 30-second, 1-minute, 2-minute, 3-minute, 5-minute, 10-minute, 15-minute, or 20-minute time-out period. The time-out period may also be more than 20 minutes.

Transmission Security may also be used to protect information. In some examples, only secure communication protocols may be allowed. In some examples, SSL-only communication may occur between a client and a platform, such as a HIPAA-compliance platform. In some examples, communications may be terminated at application servers. Additionally, in some examples, there may be no decryption/re-encryption in non-secured zones. In further examples, SSL-only communication may be used intra-platform with CA signed certificates.

In examples, servers may be secured using rotating secrets (e.g., stored on encrypted local volumes) to load secrets from a remote software security module (RSSM) using key-pair signed requests coupled with local server intrusion countermeasures to wipe ephemeral secrets, with quick manual recovery using master secrets.

Each server may run services, such as a database or a REST API, that either store PII on disk or store access credentials allowing access to PII. This method may ensure the data is stored on encrypted volumes which are mounted on startup using a rotating secret and a key-pair to make a signed, encrypted api call to a RSSM which may return a decrypted mount password (e.g., used to mount local encrypted volumes) and the next secret, which may then be saved to disk, or forgotten. If forgotten, a privileged user must manually call the RSSM key service using a master key.

Now loaded, the services may run. The API services that access the database may do so using x509 certificates. Further measures may be taken to protect credentials that could be used to access PII stored on a remote database server. The API service itself may use a key-pair and rotating secret to decrypt and retrieve an object stored at the RSSM. This object may contain the certificates required to connect to the database server and without touching the disk.

If root access is gained, scripts may run that wipe the rotating boot secret (if it exists), stop any privileged services, and unmount the encrypted volumes. In this example, it may be improbable that an attacker could retrieve the credentials required to decrypt and access any PII.

A server can be easily put back into service by synchronizing a new boot secret by calling the RSSM using a master object key. The application services, having their rotating secrets intact on the encrypted volume, can be restarted without manual intervention.

Each object at remote software security module (RSSM) may be encrypted using a master key, and once for each key-pair that accesses it. Whenever a client creates or requests an object using a new key-pair, the master password for that object may be used. The data may then be decrypted and re-encrypted with a one-time use secret that is tied to the key-pair. Each subsequent use of a key-pair may result in a new secret, which is used to make the next request. As such, each object is encrypted (n*in-use-key-pairs)+1.

A key pair consists of a public and private key. The private key is used to sign client requests using a sha256-hmac with some additional request information, server time and request nonce. The RSSM uses the public key sent by the client to authenticate the signature, and to match up the requested object with the correct locally encrypted object. The rotating secret sent by the client is then used to decrypt the object, which is then re-encrypted and stored. The decrypted data and new rotating secret are then returned to the client.

Organizations that sign up to use a HIPAA-compliance platform as provided herein may be provisioned with a unique Organization, or "Org." Data may be secured within each org, and it may be difficult to access data from other orgs or for other orgs to access data in yours. Each org is identified with an OrganizationId, and all data within your org is keyed to that Id.

Also upon sign-up, a user account may be designated as the org Administrator account. With administration privileges, you are able to administer and customize your org to suit your needs. For example, you can enable and disable your own apps and keys, customize org-wide settings such as account verification, session timeouts, or look-and-feel. You can also provision other user accounts and specify user roles, including the admin role in order to delegate administration to others.

Computer Control Systems

Figure 8:
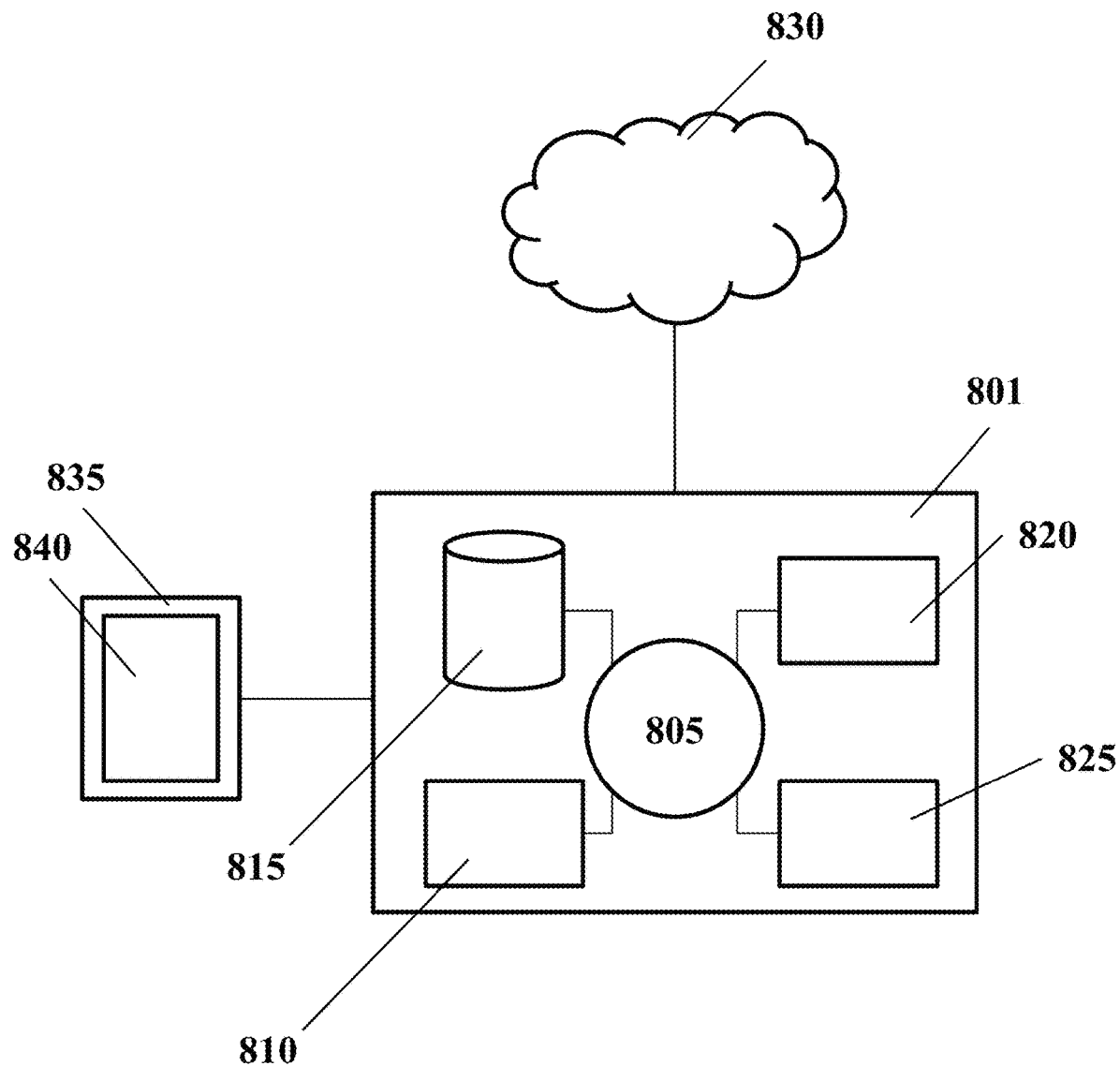
FIG. 8 shows a computer control system that is programmed or otherwise configured to implement methods provided herein.

The present disclosure provides computer control systems that are programmed to implement methods of the disclosure. FIG. 8 shows a computer system 801 that is programmed or otherwise configured to enable HIPAA compliance with respect to software applications. The computer system 801 includes a central processing unit (CPU, also "processor" and "computer processor" herein) 805, which can be a single core or multi core processor, or a plurality of processors for parallel processing. The computer system 801 also includes memory or memory location 810 (e.g., random-access memory, read-only memory, flash memory), electronic storage unit 815 (e.g., hard disk), communication interface 820 (e.g., network adapter) for communicating with one or more other systems, and peripheral devices 825, such as cache, other memory, data storage and/or electronic display adapters. The memory 810, storage unit 815, interface 820 and peripheral devices 825 are in communication with the CPU 805 through a communication bus (solid lines), such as a motherboard. The storage unit 815 can be a data storage unit (or data repository) for storing data. The computer system 801 can be operatively coupled to a computer network ("network") 830 with the aid of the communication interface 820. The network 830 can be the Internet, an internet and/or extranet, or an intranet and/or extranet that is in communication with the Internet. The network 830 in some cases is a telecommunication and/or data network. The network 830 can include one or more computer servers, which can enable distributed computing, such as cloud computing. The network 830, in some cases with the aid of the computer system 801, can implement a peer-to-peer network, which may enable devices coupled to the computer system 801 to behave as a client or a server.

The CPU 805 can execute a sequence of machine-readable instructions, which can be embodied in a program or software. The instructions may be stored in a memory location, such as the memory 810. The instructions can be directed to the CPU 805, which can subsequently program or otherwise configure the CPU 805 to implement methods of the present disclosure. Examples of operations performed by the CPU 805 can include fetch, decode, execute, and writeback.

The CPU 805 can be part of a circuit, such as an integrated circuit. One or more other components of the system 801 can be included in the circuit. In some cases, the circuit is an application specific integrated circuit (ASIC).

The storage unit 815 can store files, such as drivers, libraries and saved programs. The storage unit 815 can store user data, e.g., user preferences and user programs. The computer system 801 in some cases can include one or more additional data storage units that are external to the computer system 801, such as located on a remote server that is in communication with the computer system 801 through an intranet or the Internet.

The computer system 801 can communicate with one or more remote computer systems through the network 830. For instance, the computer system 801 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 801 via the network 830.

Methods as described herein can be implemented by way of machine (e.g., computer processor) executable code stored on an electronic storage location of the computer system 801, such as, for example, on the memory 810 or electronic storage unit 815. The machine executable or machine readable code can be provided in the form of software. During use, the code can be executed by the processor 805. In some cases, the code can be retrieved from the storage unit 815 and stored on the memory 810 for ready access by the processor 805. In some situations, the electronic storage unit 815 can be precluded, and machine-executable instructions are stored on memory 810.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 801 can include or be in communication with an electronic display 835 that comprises a user interface (UI) 840. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 805. The algorithm can, for example, determine whether an application is HIPAA compliant.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for determining whether a software application, executing on an electronic device, is compliant with the Health Insurance Portability and Accountability Act (HIPAA), the method comprising:

receiving, over a computer network and at a computing system including a processor, a request to determine whether the software application is compliant with HIPPA, wherein the software application has access to a data object that includes at least protected health information (PHI) or personally identifiable information (PII);

determining, by the processor, whether a threshold number of one or more access control safeguard techniques is implemented for the data object by the software application;

determining, by the processor, whether a threshold number of one or more audit control safeguard techniques is implemented for the data object by the software application;

determining, by the processor, whether a threshold number of data integrity safeguard techniques is implemented, for the data object, by the software application;

determining, by the processor, whether a threshold number of one or more authentication safeguard techniques is implemented for the data object by the software application;

determining, by the processor, whether a threshold number of one or more transmission security safeguard techniques is implemented for the data object by the software application;

determining that the software application is compliant with HIPAA in response to determining that the software application implements (1) the threshold number of the one or more access control safeguard techniques, (2) the threshold number of the one or more audit control safeguard techniques, (3) the threshold number of the one or more data integrity safeguard techniques, (4) the threshold number of the one or more authentication safeguard techniques, and (5) the threshold number of the one or more transmission security safeguard techniques; and outputting, on a user interface, an indication indicating that the software application is compliant with HIPAA or not compliant with HIPAA.

2. The method of claim 1, wherein said software application is a mobile application.

3. The method of claim 1, wherein said software application is a web-based application.

4. The method of claim 1, further comprising providing remedial measures to modify operation of the software application from being not complaint with HIPAA to being compliant with HIPAA.

5. The method of claim 1, wherein the user interface is associated with the software application.

6. The method of claim 1, wherein the one or more access control safeguard techniques include one or more of (1) a unique user identification safeguard technique that is implemented for the data object, (2) an emergency access procedure safeguard technique that is implemented for the data object, (3) an automatic logoff safeguard technique that is implemented for the data object, (4) an encryption/decryption safeguard technique that is implemented for the data object, (5) an assigned roles safeguard technique that is implemented for the data object, or (6) an access control list safeguard technique that is implemented for the data object.

7. The method of claim 6, wherein the emergency access procedure safeguard technique includes generating incremental backups of the data object at predetermined periods of time.

8. The method of claim 7, wherein incremental backups of the data object are performed at a predetermined period of time selected from the group consisting of two hours, four hours, six hours, and eight hours.

9. The method of claim 6, wherein said emergency access procedure safeguard technique includes the data object being recoverable within a predetermined period of time.

10. The method of claim 1, wherein the one or more data integrity safeguard techniques include one or more of (1) a transparent encryption safeguard technique implemented for the data object, (2) an e-tag safeguard technique implemented for the data object, or (3) a signed request safeguard technique for a transfers of the data object.

11. The method of claim 1, wherein the one or more authorization safeguard technique include performing a procedure to verify that a user or an entity accessing the data object is authentic.

12. The method of claim 11, wherein the procedure includes verifying one or more of (1) a unique user identifier assigned to the user or the entity, can email address associated with the user or the entity, or (3) a mobile number associated with the user or the entity.

13. The method of claim 11, wherein the procedure includes verifying a device fingerprint for a device utilized by the user or the entity.

14. A non-transitory computer readable medium comprising machine executable code that, upon execution by one or more computer processors of a computing device, cause the computing device to perform operations comprising:

receiving a request to determine whether a software application is compliant with the Health Insurance Portability and Accounting Act (HIPAA), wherein the software application has access to a data object that includes at least protection health information (PHI) or personally identifiable information (PII);

determining whether a threshold number of one or more access control safeguard techniques is implemented for the data object by the software application;

determining whether a threshold number of one or more audit control safeguard techniques is implemented for the data object by the software application;

determining whether a threshold number of data integrity safeguard techniques is implemented for the data object by the software application;

determining whether a threshold number of one or more authentication safeguard techniques is implemented for the data object by the software application;

determining whether a threshold number of one or more transmission security safeguard techniques is implemented for the data object by the software application;

determining that the software application is compliant with HIPAA in response to determining that the software application implements (1) the threshold number of the one or more access control safeguard techniques, (2) the threshold number of the one or more audit control safeguard techniques, (3) the threshold number of the one or more data integrity safeguard techniques, (4) the threshold number of the one or more authentication safeguard techniques, and (5) the threshold number of the one or more transmission security safeguard techniques; and outputting an indication indicating that the software application is compliant with HIPAA or not compliant with HIPAA.

15. The non-transitory computer-readable medium of claim 14, wherein the one or more access control safeguard techniques include one or more of (1) a unique user identification safeguard technique that is implemented for the data object, (2) an emergency access procedure safeguard technique that is implemented for the data object, (3) an automatic logoff safeguard technique that is implemented for the data object, (4) an encryption/decryption safeguard technique that is implemented for the data object, (5) an assigned roles safeguard technique that is implemented for the data object, or (6) an access control list safeguard technique that is implemented or the data object.

16. The non-transitory computer-readable medium of claim 15, wherein the emergency access procedure safeguard technique includes generating incremental backups of the data object at predetermined periods of time.

17. A system for determining whether a software application, executing on an electronic device, is compliant with the Health Insurance Portability and Accountability Act (HIPAA), the system comprising:
   a processor coupled to a memory, the processor configured to:
      receive, over a computer network, a request to determine whether the software application is compliant with HIPPA, wherein the software application has access to a data object that includes at least protected health Information (PHI) or personally identifiable information (PII);
      determine whether a threshold number of one or more access control safeguard techniques is implemented for the data object by the software application;
      determine whether a threshold number of one or more audit control safeguard techniques is implemented for the data object by the software application;
      determine whether a threshold number of one or more data integrity safeguard techniques is implemented for the data object by the software application;
      determine whether a threshold number of one or more authentication safeguard techniques is implemented for the data object by the software application;
      determine whether a threshold number of one or more transmission security safeguard techniques is implemented for the data object by the software application;
      determine that the software application is compliant with HIPPA in response to determining that the software application implements (1) the threshold number of the one or more access control safeguard techniques, (2) the threshold number of the one or more audit control safeguard techniques, (3) the threshold number of the one or more data integrity safeguard techniques, (4) the threshold number of the one or more authentication safeguard techniques, and (5) the one or more transmission security safeguard techniques; and
      output, on a user interface, an indication indicating that the software application is complaint with HIPAA or not compliant with HIPAA.

18. The system of claim 17, wherein the processor is further configured to provide remedial measures to modify operation of the software application from being not compliant with HIPAA to being compliant with HIPAA.

19. The system of claim 17, wherein the processor is further configured to output the indication on a user interface of an electronic device of a user.

20. The system of claim 17, wherein the one or more access control safeguard techniques include one or more of (1) a unique user identification safeguard technique that is implemented for the data object, (2) an emergency access procedure safeguard technique that is implemented for the data object, (3) an automatic logoff safeguard technique that is implemented for the data object, (4) an encryption/decryption safeguard technique that is implemented for the data object, (5) an assigned roles safeguard technique that is implemented for the data object, or (6) an access control list safeguard technique that is implemented for the data object.

21. The system of claim 20, wherein the emergency access procedure safeguard technique includes generating incremental backups of the data object at predetermined periods of time.

* * * * *